(12) United States Patent
Opitz et al.

(10) Patent No.: US 6,653,142 B1
(45) Date of Patent: Nov. 25, 2003

(54) AUTOMATIC DETERMINATION OF THE CONTAMINATION OF AQUEOUS CLEANING SOLUTIONS WITH CARBONACEOUS COMPOUNDS

(75) Inventors: Werner Opitz, Langenfeld (DE); Hans-Willi Kling, Wuppertal (DE); Andrea Wimschneider, Duesseldorf (DE); Ibolya Bartik-Himmler, Odenthal (DE); Bernd Schenzle, Troy, MI (US); Wolfgang Krey, Wuppertal (DE)

(73) Assignee: Henkel Kommanditgesellschaft auf Aktien (Henkel KGaA), Duesseldorf (DE)

( * ) Notice: Subject to any disclaimer, the term of this patent is extended or adjusted under 35 U.S.C. 154(b) by 0 days.

(21) Appl. No.: 09/674,599

(22) PCT Filed: Apr. 30, 1999

(86) PCT No.: PCT/EP99/02941
§ 371 (c)(1), (2), (4) Date: Mar. 29, 2001

(87) PCT Pub. No.: WO99/58969
PCT Pub. Date: Nov. 18, 1999

(30) Foreign Application Priority Data

May 9, 1998 (DE) .......................................... 198 20 800

(51) Int. Cl.⁷ ................................................ G01N 33/00
(52) U.S. Cl. .................. 436/146; 436/55; 436/103; 436/104; 436/142; 436/133
(58) Field of Search .................... 422/3, 7, 15; 436/55, 436/103, 104, 181, 146, 142

(56) References Cited

U.S. PATENT DOCUMENTS

| | | | |
|---|---|---|---|
| 3,530,292 A | * 9/1970 | Hill | 436/146 |
| 3,675,227 A | * 7/1972 | Fukasawa et al. | 340/521 |
| 3,680,579 A | * 8/1972 | Hisada et al. | 137/804 |
| 3,759,387 A | * 9/1973 | Drayton, Jr. | 210/98 |
| 3,854,881 A | 12/1974 | Cohen | 23/253 |
| 3,904,364 A | * 9/1975 | Dodson | 436/146 |
| 4,207,450 A | 6/1980 | Mittleman | 250/343 |
| 4,277,438 A | * 7/1981 | Ejzak | 422/80 |
| 4,321,545 A | * 3/1982 | Cameron | 324/442 |
| 4,590,374 A | 5/1986 | Brewster | 250/338.1 |
| 4,705,456 A | * 11/1987 | Gardeen | 417/7 |
| 4,887,453 A | * 12/1989 | Carter et al. | 73/1.03 |
| 5,224,051 A | * 6/1993 | Johnson | 700/169 |
| 5,265,031 A | * 11/1993 | Malczewski | 702/24 |
| 5,312,756 A | 5/1994 | Jolly | 436/8 |
| 5,503,682 A | * 4/1996 | Mueller-Kirschbaum et al. | 134/2 |
| 5,677,190 A | 10/1997 | Melanson et al. | 436/141 |
| 5,688,660 A | * 11/1997 | Siquet-Descans | 435/29 |
| 6,143,568 A | * 11/2000 | Pilz | 436/62 |

FOREIGN PATENT DOCUMENTS

| | | | |
|---|---|---|---|
| DE | 32 23 167 | 12/1983 | |
| DE | 39 09 240 | 9/1990 | |
| DE | 44 05 881 | 8/1995 | |
| DE | 196 10 855 | 9/1997 | |
| JP | 08/089638 | 4/1996 | |
| JP | 09/072894 | 3/1997 | |
| JP | 09089638 A | * 4/1997 | G01G/17/04 |
| JP | 10/177016 | 6/1998 | |

OTHER PUBLICATIONS

Patent Abstracts of Japan, vol. 1998, No. 11.
Patent Abstracts of Japan, vol. 1997, No. 07.
Patent Abstracts of Japan, vol. 1997, No. 08.
DIN 38409.
Fabinski et al., Die kontinuierliche On–Line–Messung des organischen Kohlenstoffs und des gebundenen Stickstoffs in Ab–und ProzeBwaessern mit dem Tocas, GWF 134 (10): 1993 pp. 613–619.

* cited by examiner

*Primary Examiner*—Jill Warden
*Assistant Examiner*—Yalena Gakh
(74) *Attorney, Agent, or Firm*—Stephen D. Harper

(57) ABSTRACT

A method of automatically determining the content of inorganic carbon and/or total organic carbon in an aqueous purifying solution wherein, in program-controlled manner, (a) a sample of a predetermined volume is taken from the aqueous purifying solution; (b) if desired, the sample is freed of solids and/or homogenized; (c) if desired, the sample is diluted with water in a ratio which has been preset or is determined as a result of a preliminary analysis; (d) the inorganic carbon and/or total organic carbon is analysed using known methods; and (e) the result of the analysis is transmitted to a remote location and output and/or stored on a data carrier and/or used as the basis of further calculations. Program-controlled or automatic, externally-initiated checking of the measuring device is provided. Bath treatment measures may be implemented in program-controlled manner or in response to external triggering.

24 Claims, No Drawings

AUTOMATIC DETERMINATION OF THE CONTAMINATION OF AQUEOUS CLEANING SOLUTIONS WITH CARBONACEOUS COMPOUNDS

FIELD OF THE INVENTION

This invention relates to a method of automatically monitoring and controlling purifying baths wherein the content of inorganic carbon (IC) or total organic carbon (TOC) or the sum thereof (total carbon TC) in the aqueous purifying solution is determined as measurement and control parameters. The method is conceived in particular for commercial purifying baths in the metal-processing industry and, for example, in automobile construction. It permits, for example, automatic monitoring of the loading of the purifying bath, in particular with fats and oils, characterised by the parameter TOC, and if necessary the supplementation of the purifying bath or the initiation of other bath treatment measures automatically or in response to an external request. The method has been conceived in particular such that the analysis results are transmitted to a location remote from the purifying bath. Furthermore, it is possible to intervene in the automatic measurement process or initiate the refilling or other bath treatment measures from a: location remote from the purifying bath. The "location remote from the purifying bath" may be situated in a superordinate process control system, in a control center of the plant in which the purifying bath is situated, or also at a location outside the plant.

BACKGROUND OF THE INVENTION

The purification of metal components prior to further processing thereof constitutes a routine task in the metal-processing industry. The metal components may be contaminated, for example, with temporary coatings which have dissolved away or leached out, pigment dirt, dust, metal rubbings, corrosion protection oils, jointing materials such as adhesive residues, cooling lubricants or deformation agents. Prior to the further processing, in particular prior to a corrosion protection treatment or coating (for example phosphation, chromatization, anodization, reaction with complex fluorides, organic coating etc) or prior to lacquering, these impurities must be removed by means of a suitable purifying solution. Spraying, dipping or combined processes may be used for this purpose.

Industrial purifiers in the metal-processing industry are generally alkaline (pH above 7, for example 9 to 12), but may also be acidic. The basic constituents of alkaline purifiers are alkalis (alkali hydroxides, -carbonates, -silicates, -phosphates, -borates) as well as non-ionic and/or anionic surfactants. As additional auxiliary components, the purifiers frequently and/or anionic surfactants. As additional auxiliary components, the purifiers frequently contain complex-forming agents (gluconates, polyphosphates, salts of amino acids such as ethylene diamine tetraacetate or nitrilotriacetate, salts of phosphonic acids, such as salts of hydroxyethane diphosphonic acid, phosphono-butane tricarboxylic acid or other phosphonic or phosphonocarboxylic acids), corrosion protection means, such as salts of carboxylic acids having 6 to 12 carbon atoms, alkanolamines and foam inhibitors, such as alkoxylates of alcohols having closed end groups and 6 to 16 carbon atoms in the alkyl group. If the purifying baths contain no anionic surfactants, cationic surfactants may also be used. Acidic purifiers contain acids, such as phosphoric acid or sulfuric acid, in place of the alkalis.

As non-ionic surfactants, the purifiers generally contain ethoxylates, propoxylates and/or ethoxylates/propoxylates of alcohols or alkylamines having 6 to 16 carbon atoms in the alkyl group, which may also have closed end groups. Alkylsulfates and alkylsulfonates are widely used as anionic surfactants. Alkylbenzene sulfonates are also encountered, although these are disadvantageous from the environmental standpoint. In particular, cationic alkylammonium compounds containing at least one alkyl group having 8 or more carbon atoms are suitable as cationic surfactants.

SUMMARY OF THE INVENTION

As a result of the purifying process, the dirt constituents which have dissolved away from the surfaces accumulate in the purifying solution. Pigment dirt may lead to loading with inorganic carbon. Corrosion protection oils, cooling lubricants or deformation agents, such as drawing grease and/or organic coatings which have dissolved away or leached out or jointing materials, lead to the loading of the purifying solution with total organic carbon. As the majority of this total organic carbon is present in the form of mineral oils, mineral fats, or oils and fats of animal or vegetable origin, it is often referred to in abbreviated form as the "fat loading" of the purifying solution. The majority of such oils and fats are present in emulsified form in the purifying solution. Oils and fats of animal or vegetable origin may, however, be at least partially hydrolysed by an alkaline purifying solution. The hydrolysis products may then also occur in dissolved form in the purifying solution. Having too high a TOC loading of the purifying solution, it is no longer guaranteed that the purifying solution will free the components to be purified of oils and fats to the required extent. Alternatively, the danger exists that oils and fats will be drawn back onto the purified components when these are removed from the purifying solution. Therefore. it is necessary to maintain the fat loading of the purifying solution below a critical maximum value which may depend upon the further use of the purified components and upon the composition of the purifying solution. In the case of a high fat loading, it is possible to increase the surfactant content of the purifying solution in order to increase the fat dissolving capacity of the purifying solution. Alternatively, bath treatment measures are initiated with the goal of reducing the fat loading of the purifying Solution. This is any case necessary at a predetermined maximum limit of the fat loading. In the simplest case, the purifying solution is entirely or partially discarded and replaced or supplemented with fresh purifying solution. However, on account of the waste water thereby produced and due to the need for fresh water, it is endeavoured to separate fats and oils from the purifying solution and to continue to use the purifying solution, optionally supplemented with active ingredients. Suitable devices for this purpose, such as separators or membrane filtration apparatus, are known in tile art.

Previously, the purifying efficiency of a purifying solution was conventionally assessed visually on the basis of the purification result. The plant operating personnel assess the purifying efficiency and implement the required measures, such as bath supplementation or bath renewal. This currently customary method requires that operating personnel remain in the vicinity of the purifying bath at the required monitoring times. The shorter the desired monitoring interval, the greater the demands upon the operating personnel for the visual assessment.

DETAILED DESCRIPTION OF THE INVENTION

By way of contrast, an object of the present invention is to implement and document the monitoring of purifying baths by determining the content of inorganic carbon and/or total organic carbon in an automated manner such that at least the results of the analysis are stored on a data carrier and/or output. Preferably, the measuring device used is to be self-checking and self-calibrating and, in the case of a malfunction, is to transmit an alarm signal to a remote location. Furthermore, it is preferably to be possible to check the functioning capability of the measuring device and the measurement results from a remote location. Furthermore, it is to be possible to intervene in the measurement process and the bath treatment measures from a remote location. By virtue of the desired remote monitoring, the outlay in terms of personnel for tile bath monitoring and bath control of tile purifying baths is to be reduced.

This object is achieved by a method for automatically determining the content of inorganic carbon and/or total organic carbon in an aqueous purifying solution wherein, in a program controlled manner:
(a) a sample of a predetermined volume is taken from the aqueous purifying solution;
(b) if desired, the sample is freed of solids and/or homogenized;
(c) if desired, the sample is diluted with water in a ratio which has been preset or is determined as a result of a preliminary analysis;
(d) the inorganic carbon and/or total organic carbon is analysed using known methods; and
(e) the result of the analysis is transmitted to a remote location and output and/or stored on a data carrier and/or used as the basis of further calculations.

The sample volume taken in (a) may be permanently programmed into the control section of the measuring device to be used for the method. Preferably the size of the sample volume may be changed from a remote location. Additionally, the control program may be designed such that it makes the sample volume to be used dependent upon the result of a previous measurement and/or automatically dilutes the sample to a desired measurement range. For example, the sample volume may be selected to be the greater, the lower the fat loading of the purifying bath. The accuracy of the analysis may thus be optimized.

Where the method according to the present invention refers to a "remote location", this is to be understood as a location situated not in direct contact, or at least not in visual contact, with the purifying bath. The remote location may for example be a central process control system which, as part of a total process for the surface treatment of tile metal components, monitors and controls the purifying bath as a subsidiary task. The "remote location" may also be an observation control center from which the overall process is monitored and controlled and which is situated for example in a different room to the purifying bath. The "remote location" may also, however, consist of a location outside the plant in which the purifying bath is situated. In this way, it is possible for specialists present outside the plant in which the purifying bath is situated to check and control the purifying bath. As a result, the presence of specialist personnel at the location of the purifying bath is less frequently necessary.

Suitable data lines via which the analysis results and control commands may be transmitted are available in the prior art.

Between the taking of the sample and the actual measurement it may be desirable to free the sample of solids in the optional step (b). This is unnecessary in the case of a purifying bath having only a low solids loading. However, too high a solids content of the purifying bath may lead to obstruction of valves of the measuring device. Therefore it is advisable to remove solids from the sample. This may take place automatically by filtration or also by the use of a cyclone or centrifuge. It is advisable to homogenize the sample, for example by vigorous stirring. This leads to a uniform and fine distribution of the organic impurities possibly present in the form of coarse oil or fat droplets.

If necessary, in (c), the sample is diluted using water in a specified ratio. This ratio may be fixed, but modifiable from a remote location. However, the dilution ratio may also be made dependent upon the result of a previous analysis of the content of inorganic carbon and/or total organic carbon. This ensures that the carbon content of the sample solution is in a range which permits optimal analysis using the selected method.

In (d), the inorganic carbon and/or total organic carbon may be analysed, for example by converting it into $CO_2$ and quantitatively determining the formed $CO_2$.

The conversion of the carbon into $CO_2$ by oxidation may be effected, for example, by combustion at an elevated temperature in the gas phase. The elevated temperature during the combustion is preferably greater than about 600° C., for example is about 680° C. Preferably, the combustion is carried out using air or oxygen gas in a reaction pipe aided by a catalyst. Suitable catalysts are, for example, noble metal oxides or other metal oxides, such as vanadates, vanadium oxides, chromium-, manganese- or iron oxides. Platinum or palladium deposited on aluminum oxide may also be used as catalyst. This process directly provides a $CO_2$-containing combustion gas whose $CO_2$ content may be determined as described in the following.

As an alternative to combustion in the gas phase, the conversion of the carbon into $CO_2$ may also be effected by means of wet chemistry. Here, the carbon of the sample is oxidized using a strong chemical oxidant, such as hydrogen peroxide or peroxodisulfate. If desired, this wet-chemical oxidation reaction may be accelerated with the aid of a catalyst of the type referred to in the foregoing and/or with UV-radiation. In this case, it is preferable to expel the formed $CO_2$ with a gas flow from the, if necessary acidified, sample for quantitative determination thereof. Carbon found in the form of carbonates or $CO_2$ may likewise be detected.

Irrespective of the method by which gaseous $CO_2$ has been generated, it may be quantitatively determined in accordance with one of the following methods. When the quantity of the sample is known, the content of inorganic carbon and/or total organic carbon in the purifying solution may be calculated therefrom. Alternatively, using a predetermined conversion factor, the result of the analysis may be given in the form of fat loading per liter of purifying bath if inorganic carbon is not present or has previously been removed.

Different methods known in the prior art may be used to determine the $CO_2$ content of the obtained gas flow. For example, the gases may be passed through an absorber solution and, for example, the increase in weight of the absorber solution may be measured. For example, an aqueous solution of potassium hydroxide which absorbs $CO_2$ with the formation of potassium carbonate is suitable for this purpose. As an alternative to determining the increase in weight, it is possible to determine the change in the electrical conductivity of the absorption solution or residual alkalinity thereof following the absorption of the $CO_2$.

The formed $CO_2$ may be absorbed by a suitable solid whose increase in weight is measured. For example, soda asbestos, is suitable for this purpose. Naturally, it is necessary to replace both an absorber solution and a solid absorber when they are exhausted and are no longer able to bind $CO_2$.

However, for an automatically operating process it is simpler to quantitatively determine the $CO_2$ content of the gas by measuring the infrared absorption. The determination of the infrared absorption may take place, for example, at a wavelength of 4.26 μm corresponding to a wave number of 2349 $cm^{-1}$. Devices capable of performing the combustion of the sample and the measurement of the infrared absorption are known in the prior art. The TOC system of the company Shimadzu is mentioned as an example.

For the photometric analysis of the $CO_2$ content of the combustion gas and the gas expelled from the sample, it is possible to use not only dispersively operating infrared spectrometers, but also non-dispersive photometers. These are also known as "NDIR devices". Such a device is described, for example, in DE-A-4405881.

In this analysis method, the proportion of carbon deriving from deliberately added active ingredients in the purifying solution is also detected. Surfactants, organic corrosion inhibitors and organic complex-forming agents are mentioned as examples. However, the content thereof in purifying solution is known within specific fluctuation limits or may be separately determined. The proportion of total organic carbon deriving from these active ingredients may thus be subtracted from the result of the analysis. The proportion deriving from the entered impurities is then obtained. In practice, it is not essential in this case for the proportion of carbon present in the form of active ingredients to be taken into account in the carbon analysis. Rather, it is often sufficient to fix an upper limit of the carbon content of the purifying solution which itself takes into account the active ingredient content. By means of the carbon analysis, it is then ascertained whether the carbon loading is below or above this maximum limit.

The proportion of total organic carbon present in the form of lipophilic substances may alternatively be determined such that the lipophilic substances are extracted into an organic solvent not miscible in all proportions with water. When the solvent has evaporated off, the lipophilic substances remain and may be gravimetrically analysed. Preferably, however, the infrared absorption of the lipophilic substances in the extract is photometrically analysed. Halogenated hydrocarbons may be used in particular as organic solvent not miscible in all proportions with water. A preferred example is 1,1,2-trichlorotrifluoroethane. This analysis method is based on DIN 38409, part 17, but, in contrast to this method, the proportion of lipophilic substances in the sample is analysed not gravimetrically following the evaporation of the organic solvent, but photometrically in the organic solvent. The quantitative analysis is preferably performed as in DIN 38409, part 18, by measuring the infrared absorption of the lipophilic substances in the extract at a characteristic vibrational frequency of the $CH_2$ group. Here, it is advisable for an organic solvent which itself contains no $CH_2$ groups to be used for the extraction. The infrared absorption band at 3.42 μm (2924 $cm^{-1}$), for example, may be used for this photometric analysis. All the organic substances which contain $CH_2$ groups and may be extracted into the organic solvent are now detected. In part, these are also the surfactants in the purifying solution. If this surfactant constituent is not to be detected, it may be separately determined by an alternative method and subtracted from the total result. If necessary, the distribution coefficient of the surfactants between the purifying solution and the organic solvent not miscible in all proportions with water must be previously determined. In practice, however, it may be sufficient to fix a maximum value of the permissible loading of the purifying solution with lipophilic substances which additionally takes into account the surfactant constituents. If this maximum value is exceeded, bath treatment measures are to be initiated.

As part of this method, it is advisable to calibrate infrared spectrometers using a known quantity of a lipophilic substance. A solution of 400 to 500 mg methylpalmitate in 100 ml 1,1,2-trichlorotrifluoroethane may be used, for example, as calibrating solution. This calibrating solution is likewise used to monitor the functioning of the IR-photometer.

In this case, it is preferable to proceed by firstly adding a phosphoric acid magnesium sulfate solution to the sample of the purifying solution. This solution is prepared by dissolving 220 g crystalline magnesium sulfate and 125 ml 85 wt. % phosphoric acid in deionised water and supplementing this solution with deionised water to 1000 g. The sample solution is mixed with about 20 ml of the phosphoric acid magnesium sulfate solution. Then, 50 ml of the organic solvent not miscible in all proportions with water. preferably 1,1,2-trichlorotrifluoroethane, is added. The aqueous and organic phases are mixed, a phase separation is performed, and the organic phase is isolated. Preferably this organic phase is again washed with the phosphoric acid magnesium sulfate solution, the phase separation is again performed and the organic phase is drawn off. This is transferred into a measuring cuvette and the infrared absorption is measured at a vibrational band of the $CH_2$ group. A suitable measuring cuvette consists, for example, of a quartz glass cuvette having a coating thickness of 1 mm. By comparison with the calibration curve, which also contains the blind value of the photometer, it is possible to determine the content of lipophilic substances in the sample on the basis of the infrared absorption.

Irrespective of the type of analysis method selected, the result of the analysis is then output and/or stored on a data carrier (e). Here, the data carrier may be situated at the analysis location or in a remote computer unit. "Output of the result of the analysis" is to be understood in that the result is either forwarded to a superordinate process control system or is displayed on a screen or printed out so as to be intelligible to a human. The location at which the result is displayed or output may correspond to the "remote location" indicated above. It is preferable for the results of the individual analyses to be stored on a data carrier at least for a predetermined time interval to enable them to be evaluated subsequently, for example in the form of a quality assurance check. However, the results of the carbon analyses need not be directly output as such or stored on data carriers. Rather, they may also be used directly as the basis of further calculations, the results of these further calculations being displayed or stored. For example, in place of the instantaneous carbon content, it is also possible to display the trend of the values and/or the relative change therein. Alternatively, the instantaneous carbon contents may be converted into "% of the maximum content".

In the simplest case, the method according to the present invention operates such that (a) to (e) are repeated after a predetermined time interval. The predetermined time interval will depend upon the requirements of the operator of the purifying bath and may comprise any desired time interval from a few minutes to several days. For quality assurance, it is preferable for the predetermined time intervals to range, for example, between 5 minutes and 2 hours. For example, a measurement may be performed every 15 minutes.

However, the method according to the present invention may also be implemented in a such manner that (a) to (e) are repeated after time intervals which are the shorter, the greater the difference between the results of two consecutive analyses. The control system for the method according to the present invention may thus itself decide whether the time intervals between the individual analyses are to be reduced or increased. Naturally, the instruction as to which time intervals are to be selected in the case of which differences between consecutive analyses must be preset in the control system. It may also be provided that the measurement intervals are coupled to the results of the measurement of other contents. For example, the time intervals at which the inorganic carbon or total organic carbon in the purifying solution is measured may be made dependent upon the results of a measurement of the surfactant content. Naturally, it is also possible externally to preset variable measurement intervals correlated, for example, with the material throughput through the purifying bath and/or with the known average contamination of the material to be purified.

Furthermore, the method according to the present invention may be implemented in such a manner that (a) to (e) are performed at a desired time in response to an external request. In this way, for example, immediate monitoring of the carbon content of the purifying bath may be carried out if quality problems are ascertained in following process steps. The carbon measurement may thus take place in a time-controlled manner (at fixed time intervals) or in an event-controlled manner (upon tile ascertainment of changes or in response to external requests).

The present sampling and measuring system is preferably designed such that a central measuring unit may be supplied with samples from different purifying baths. In the relevant industrial sector, it is customary to purify metal components in a plurality of purifying baths arranged in series. By means of sample lines leading to the individual purifying baths, the carbon contents of the respective purifying solutions may be analysed consecutively using one single measuring unit. The measurement sequence of the individual baths may be preset externally. Here, different measurement intervals may be provided for the individual purifying baths so that, for example, one particular purifying bath is checked more frequently than another. Furthermore, it may be provided that the carbon content in a downstream purifying bath is not checked until the carbon content in an upstream purifying bath reaches a specified limit value.

In the implementation of the method according to the present invention, it may be desirable to detect both inorganic carbon and total organic carbon (TOC). This is the case, for example, when the sample is combusted for the analysis of the carbon content. Here, dissolved $CO_2$ or carbon in the form of carbonates is additionally detected if $CO_2$ splits off from the carbonates at the selected combustion temperature. If in this case the inorganic carbon is not to be additionally measured, it may be removed in that the sample may be acidified and the formed $CO_2$ is purged with a gas, such as air or nitrogen. This may be desirable if in a particular case only the "fat loading" of the purifying bath is to be determined. When the carbon content present in the form of lipophilic substances is determined in accordance with the above-described extraction method, inorganic carbon is automatically not detected.

It is also possible for volatile organic compounds to be eliminated from the sample prior to the implementation of (d) by expulsion with a gas, such as air or nitrogen. For example, volatile solvents may be eliminated in this way prior to the carbon analysis.

Preferably the method according to the present invention is implemented in such manner that the measuring device used is self-monitoring and if necessary self-calibrating. For this purpose, it may be provided that, after a predetermined time interval or after a predetermined number of analyses or in response to an external request, the functioning capability of the measuring device used is checked by control measurements of one or more standard solutions. The check is carried out by measuring a standard solution containing known contents of inorganic carbon and/or total organic carbon. This check is most realistic if a standard purifying solution whose composition is as close as possible to that of the purifying solution to be checked is used as standard solution. Standard solutions which do not constitute purifying solutions may likewise be used, however, for checking and/or calibration purposes.

If, during a control measurement of a standard solution, the measuring device determines a carbon content which differs from the nominal content by a minimum amount to be predetermined, the measuring device emits an alarm signal either locally or preferably at a remote location. The alarm signal may contain an intervention proposal selected by the control program of the measuring device or by the superordinate process control system.

In the method according to the present invention, it may also be provided that the functioning capability of the measuring device used is checked by a control measurement of one or more standard solutions if the results of two consecutive measurements differ by a predetermined amount. In this way, it is possible to distinguish whether established deviations in the carbon content of the purifying solution are real and necessitate bath treatment measures or whether they have been simulated by a fault in the measuring system.

Depending upon the result of the check on the measuring device used, the analyses of the content of inorganic carbon and/or total organic carbon performed between the current and the previous control measurement may be provided with a status characteristic indicating the reliability of these analyses. If, for example, consecutive control measurements for checking the measuring device used have shown that it is operating correctly, the analyses of the carbon content may be provided with a status characteristic "OK". If the results of the control measurements differ by a predetermined minimum amount, the intervening analyses may be provided, for example, with the status characteristic "doubtful".

It may additionally be provided that, depending upon the result of the check on the measuring device used, the automatic analysis of the content of inorganic carbon and/or total organic carbon is continued and/or one or more of the following actions is performed: analysis of established deviations, correction of the measuring device, termination of the analysis of the carbon content, transmission of a status signal or an alarm signal to a superordinate process control system or monitoring device, thus to a remote location. If desired, the measuring device may thus itself decide in accordance with preset criteria whether it is sufficiently capable of functioning so as to allow the carbon analyses to continue or whether deviations necessitating manual intervention are ascertained.

Preferably, the measuring system employed in the method according to the present invention is designed such that it automatically monitors the levels and/or consumption of the standard and test solutions used, as well as possible auxiliary solutions and upon the undershooting of a predetermined minimum level emits a warning signal. In this way it is possible to prevent the measuring device from becoming incapable of functioning due to a lack of the required solutions. The monitoring of the levels may take place in accordance with known methods. For example, the vessels containing the solutions may be placed on scales recording the particular weight of the solutions. Alternatively a float is inserted. Alternatively, a minimum level may be checked by means of a conductivity electrode submerged in the vessel containing tile solution. The warning signal to be emitted by the measuring device is preferably transmitted to the remote location so that the appropriate measures may be initiated from there. In general, in the method according to the present invention it is preferably provided that the results of the analyses and/or of the control measurements and/or of the calibrations and/or the status signals are transmitted to a remote location continuously or at predetermined time intervals and/or upon request. In this way, the monitoring personnel, who are not required to be present at the location of the purifying bath, are kept constantly informed about the bath's instantaneous content of inorganic carbon and/or total organic carbon and thus about the current fat- and oil loading. Depending upon the result of the analyses and control measurements, necessary corrective measures may be adopted either automatically via a process control system or by manual intervention.

The simplest corrective measure consists in that, upon the overshooting of a predetermined maximum value of inorganic carbon and/or total organic carbon or in response to an external request, a device is activated which dispenses one or more supplementary components (solution or powder) into the purifying bath. This may take place, for example, in automated fashion in that, depending upon the determined carbon content, a specified quantity of supplementary solution or supplementary powder is supplied to the purifying bath. Here it is possible to vary the size of the added portion itself or, in the case of fixed added portions, the time interval between the individual additions. This may be effected, for example, via dosing pumps or also in weight-controlled fashion. In the method according to the present invention, it is thus provided, on the one hand, that, in the case of specific deviations from the nominal value (in particular when the functioning capability of the measuring device has been ascertained by the control measurements), a specified quantity of supplementary component is additionally dosed into the purifying bath. Furthermore, it may be provided that these bath supplementing measures are performed when a predetermined minimum change in the carbon content has been established. Furthermore, however, this additional dosing may also take place in response to an external request, for example from a remote location, independently of the instantaneous carbon content. The additional dosing, for example of surfactants, increases the carbon content of the purifying solution. Upon the next analysis of the carbon content this must be taken into account in an appropriate manner, which may take place automatically. An addition of surfactants increases the oil- and fat-bearing capacity of the purifying bath. Accordingly, it is necessary to Increase the tolerable maximum value of the carbon loading, the overshooting of which initiates the next bath treatment measure. This may be provided automatically in the control program.

In place of an additional dosing of bath components, such as surfactants, or upon the overshooting of a predetermined maximum content of inorganic carbon and/or total organic carbon, bath treatment measures may be initiated to reduce the content of inorganic carbon and/or total organic carbon in the purifying solution. Such bath treatment measures have the goal in particular of reducing the fat and oil content of the purifying solution. In the simplest example, this may take place in that the purifying solution is completely or partially discharged and replaced by fresh purifying solution. It is more economical, however, to remove oils and fats from the purifying solution by measures known in the prior art, such as separation by a separator or separation by membrane filtration. As surfactants are also at least partially discharged in these processes, the purifying solution must be supplemented appropriately. The initiation of these measures may also be made dependent not only upon the absolute carbon content of the purifying solution but also upon a predetermined change in the carbon content.

Naturally, the method according to the present invention requires that the appropriate device is available. This contains a control unit, for example a computer control unit, which controls the measurement process in a time- and/or event-dependent manner. It must also comprise the required vessels for solutions, pipelines, valves, dosing- and measuring devices etc. for the control and measurement of the sample flows. The materials are to be adapted to the purpose of use, for example are to consist of high-grade steel and/or plastics. The control electronics unit of the measuring device is to possess an appropriate input-output interface to permit communication with a remote location.

The method according to the present invention, on the one hand, enables the carbon content of purifying baths to be checked on site and predetermined corrective measures to be initiated without manual intervention. In this way, the process reliability is improved and a constantly reliable purification result is obtained. Deviations from the nominal values may be detected at an early point in time and corrected automatically or manually before the purification result is impaired. On the other hand, the measurement data are preferably transmitted to a remote location so that operating or supervisory personnel are kept constantly informed about the state of the purifying bath, even when they are not present in the direct vicinity of the bath. The outlay in terms of personnel for monitoring and controlling the purifying bath may thus be considerably reduced. The documentation of the data collected in the method according to the present invention complies with the requirements of modern quality assurance. The consumption of chemicals may be documented and optimized.

What is claimed is:

1. A method of maintaining a clear efficiency and adjusting the fat loading capacity of an aqueous purifying solution by automatically determining the content of inorganic carbon and/or total organic carbon in the aqueous purifying solution wherein, in a program-controlled manner said method comprises the steps of, (a) taking a sample of a predetermined volume from the aqueous purifying solution, (b) if desired, freeing the sample of solids and/or homogenizing the sample, (c) if desired, diluting the sample with water in a ratio which has been preset or determined as a result of a preliminary analysis, (d) monitoring the total fat and oil loading of said solution by analyzing the inorganic carbon and/or total organic carbon of said solution using known methods as an indicator of a fat and oil loading of said solution, (e) transmitting the result of the analysis of step (d) to a remote location and outputting said result and/or storing said result on a data carrier and/or using said result as the basis of further calculations, and f1) activating a device and dosing one or more supplementary components into the purifying solution to increase a total fat and oil loading capacity of said solution upon the overshooting of a given maximum value or upon a given change in the content of inorganic and/or total organic carbon or upon request, or f2) removing fat and oil from the solution and reducing the content of inorganic and/or total organic carbon in the purifying solution upon the overshooting of a given maximum value or upon a given change in the content of inorganic and/or total organic carbon.

2. A method as claimed in claim 1, wherein sub-step (d) comprises analyzing inorganic carbon and/or total organic carbon by converting the carbon of the sample into $CO_2$ and quantitatively determining the formed $CO_2$.

3. A method as claimed in claim 2, wherein sub-step (d) comprises quantitatively determining the $CO_2$ absorbed in an absorber solution or a solid absorber and measuring at least one of the following variables: change in electrical conductivity, residual alkalinity, increase in weight.

4. A method as claimed in claim 2, wherein sub-step (d) comprises quantitatively determining the $CO_2$ by measuring the infrared absorption.

5. A method as claimed in claim 4, comprising measuring the infrared absorption at a wavelength of 4.26 μm corresponding to a wave number of 2349 $cm^{-1}$.

6. A method as claimed in claim 4, wherein a non-dispersive photometer is used to measure the infrared absorption.

7. A method as claimed in claim 1, wherein sub-step (d) comprises extracting lipophilic substances from said solution into an organic solvent not miscible in all proportions with water and gravimetrically analyzing said lipophilic substances by vaporising off the solvent or photometrically analyzing by infrared absorption of the lipophilic substances in the extract.

8. A method as claimed in claim 7, wherein the infrared absorption of the lipophilic substances in the extract is measured at a characteristic oscillating frequency of the $CH_2$ group.

9. A method as claimed in claim 1, comprising repeating sub-steps (a) to (e) after a predetermined time interval.

10. A method as claimed in claim 1, comprising repeating sub-steps (a) to (e) after time intervals which are the shorter, the greater the difference between the results of two consecutive analyses.

11. A method as claimed in claim 1, comprising performing sub-steps (a) to (e) in response to an external request.

12. A method as claimed in claim 1, wherein in order to determine the content of total organic carbon, prior to sub-step (d) inorganic carbon is removed from the sample by acidifying the sample and expelling the formed $CO_2$ with a gas.

13. A method as claimed in claim 1, wherein prior to sub-step (d) volatile organic compounds are removed from the sample by expulsion with a gas.

14. A method as claimed in claim 1, wherein after a predetermined time interval or after a predetermined number of analyses or in response to an external request, the functioning capability of an analyzing device used is checked by a control measurement of one or more standard solutions.

15. A method as claimed in claim 14, wherein, depending upon the result of the check of the measuring device used, the analyses of the content of inorganic carbon and/or total organic carbon performed between tie current and the previous control measurement are provided with a status characteristic indicating the reliability of these analyses of the content of inorganic carbon and/or total organic carbon.

16. A method as claimed in claim 14, wherein, depending upon the result of the check of the measuring device used, the automatic analysis of the content of inorganic carbon and/or total organic carbon is continued and/or one or more of the following actions is performed: analysis of established deviations, correction of the measuring device, termination of tile analyses of the content of inorganic carbon and/or total organic carbon, transmission of a status message or alarm signal to a superordinate process control system or to a monitoring device.

17. A method as claimed in claim 1, wherein the functioning capability of an analyzing device used is checked by a control measurement of one or more standard solutions when the results of two consecutive measurements differ by a predetermined amount.

18. A method as claimed in claim 1, comprising automatically monitoring the levels and/or consumption of the solutions used and emitting a warning signal upon the undershooting of a predetermined minimum level.

19. A method as claimed in claim 1, comprising transmitting the results of the analyses and/or of the control measurements and/or of the calibrations and/or the status signals continuously or at predetermined time intervals and/or upon request to a location different to the analysis location.

20. The method of claim 1, wherein said step f2) further comprises reducing the fat and oil content of said solution when said measured inorganic and/or total organic carbon content of said solution is above a predetermined value.

21. The method of claim 1, wherein said method maintains said total fat and oil content of said solution below a predetermined level.

22. The method of claim 1, wherein said method step f1) adds a surfactant to said solution to increase the fat loading capacity of said solution when said total organic carbon content of said solution is above a predetermined level.

23. The method of claim 1, wherein said step f2) removes the fat and oil from the solution by a membrane filtration device.

24. The method of claim 1, wherein said step f1) adds water to said solution to dilute said solution and increase said fat and oil loading capacity.

* * * * *

UNITED STATES PATENT AND TRADEMARK OFFICE
CERTIFICATE OF CORRECTION

PATENT NO.    : 6,653,142 B1
DATED         : November 25, 2003
INVENTOR(S)   : Opitz et al.

It is certified that error appears in the above-identified patent and that said Letters Patent is hereby corrected as shown below:

Column 10,
Line 39, delete "clear", and insert therefore -- cleaning --.

Column 12,
Line 4, delete "tie", and insert therefore -- the --.
Line 15, delete "tile", and insert therefore -- the --.

Signed and Sealed this

Nineteenth Day of October, 2004

JON W. DUDAS
*Director of the United States Patent and Trademark Office*